United States Patent [19]

Rickards

[11] Patent Number: 4,462,411
[45] Date of Patent: Jul. 31, 1984

[54] EVOKED RESPONSE AUDIOMETER

[75] Inventor: Field W. Rickards, Glen Iris, Australia

[73] Assignee: The University of Melbourne, Parkville, Australia

[21] Appl. No.: 337,397

[22] Filed: Jan. 6, 1982

[30] Foreign Application Priority Data

Jan. 7, 1981 [AU] Australia .............................. PE7169

[51] Int. Cl.³ .............................................. A61B 5/04
[52] U.S. Cl. .................................... 128/746; 128/731
[58] Field of Search ......................... 128/746, 731–732

[56] References Cited

U.S. PATENT DOCUMENTS 3,892,227  7/1975  Coursin et al. ................. 128/746 X
3,901,215  8/1975  Jolin ................................. 128/746 X
4,275,744  6/1981  Thornton et al. .............. 128/746 X

OTHER PUBLICATIONS

Gibson, W. P. R., "Essentials of Clinical Electric Response Audiometry", Churchhill Livingston, 1978, London & N.Y., pp. 7, 25-26, 32-33, 160-165.
Krogh, H. J., "Portable Programmable Equipment for Electric Response Audiometry", MBE & Computing, V. 15, 1977, pp. 179–183.

Primary Examiner—Kyle L. Howell
Assistant Examiner—Francis J. Jaworski
Attorney, Agent, or Firm—Dennison, Meserole, Pollack & Scheiner

[57] ABSTRACT

An evoked response audiometer is disclosed in which the patient is presented with a continuous auditory signal which is amplitude modulated and the evoked brain potentials of the patient (EEG) are recorded. The potentials are amplified and filtered and are averaged over a number of sampling periods to improve the signal to the noise ratio. The averaged signals are then analysed to determine the amplitude and phase of the main components of the response to determine whether phase locking has occurred. The phase of the main components is then plotted against variation of the modulating frequency and the gradient of the plot provides the latency of the response from which neurological and other factors of significance to the hearing of the patient may be determined. The sound pressure level of the auditory signal is also varied and the amplitude and phase of the response plotted against these changes to provide an indication of the sensitivity of the hearing of the patient.

10 Claims, 5 Drawing Figures

| △ | LEFT EAR | 24 Hz MODULATION | CARRIER FREQ. 500 Hz |
| ▲ | RIGHT EAR | 24 Hz MODULATION | CARRIER FREQ 500 Hz |
| ⊠ | LEFT EAR | 64 Hz MODULATION | CARRIER FREQ 1000 Hz |
| ⊡ | RIGHT EAR | 64 Hz MODULATION | CARRIER FREQ 1000 Hz |

EVOKED RESPONSE AUDIOMETER

This invention relates to an improved evoked response audiometer.

BACKGROUND OF THE INVENTION

The diagnosis of deafness at an early age is most important to enable the early fitting of hearing aids and in the application of educational programs to assist language development in the hearing impaired child. Current procedures in the early diagnosis of deafness include the "Cribogram" and brain stem evoked response but neither has yet been developed to a stage where they can be implemented on a wide spread basis. At present, the earliest age for diagnosis of deafness is about seven to nine months, with the average being about 2 years of age.

Auditory evoked potentials recorded from the scalp in humans have now been described in many studies. These potentials have been classified into three main groups. These groups are:

(i) the brain stem evoked potentials which are approximately 0.5 microvolts in amplitude and occur within the first 10 milliseconds following an abrupt sound stumulus, usually a click;

(ii) middle latency responses which are approximately two microvolts in amplitude and occur between 7 and 50 msecs following the presentation of a click or tone pips and, (iii) slow responses, about 10 microvolts in amplitude, following the onset of a tone burst and have latencies between 50 and 500 msecs.

Currently, the brain stem potential is receiving most attention both as a neurological and an audiological tool. It does, however, have the disadvantage of using abrupt stimuli. This is necessary since this response reflects synchronous firing patterns in the auditory pathway in the brain stem. Stimuli of slower onset fail to achieve the synchrony necessary for the recording of the various peaks. As a result of this limitation only high frequency hearing information is measured.

SUMMARY OF THE INVENTION

It is the object of the present invention to provide an improved evoked response audiometer which should facilitate the early diagnosis of deafness in a manner which should enable implementation of deafness diagnosis procedures on a wide spread basis.

The invention provides an evoked response audiometer comprising means for supplying to the patient under investigation an auditory signal and means for recording evoked brain potentials generated by said signal, characterized in that said auditory signal is presented in a continuous modulated form for an extended period of time to evoke phase-locked steady state potentials in the brain.

The audiometer of the present invention enables the recordal of the very small electrical potentials generated by the brain in response to modulated sounds and our research has shown that these potentials can correlate with the hearing threshold level of the patient under investigation. The audiometer embodying the present invention has the advantage over the prior art techniques of brain stem audiometry in that the acoustic stimuli are frequency specific whereas in the known brain stem evoked response transient acoustic stimuli are used which have a broad acoustic spectrum.

The auditory signal is preferably amplitude modulated although other forms of modulation, such as frequency modulation and beats may be used with acceptable results.

The brain potentals are preferably recorded by means of electrodes on the vertex and on the mastoids of the patient. In the preferred embodiment, the patient is presented with a continuous sinusoidally amplitude modulated tone. The brain activity is recorded for four cycles of modulation to cover substantially all frequencies within the hearing range, and the modulated wave form is used to synchronise brain activity with the acoustic stimulus thus enabling an averaging process to take place and improving the signal to noise ratio of the brain response. The average response is preferably Fourier analysed and relevant spectral components used to measure hearing loss.

The invention also provides a method of objectively testing the hearing of a patient comprising the steps of presenting to the patient for an extended period of time an auditory signal having a continuous modulated form, recording the brain potentials evoked by said signal, and analysing said potentials to determine whether they are phase-locked steady state potentials.

Preferably the signal is amplitude modulated.

As will be described in greater detail below, the potentials are preferably further recorded for changes in the frequency of modulation and changes in sound pressure level, and recorded potentials further analysed to determine response latency and hearing sensitivity.

DESCRIPTION OF PREFERRED EMBODIMENT

Figure 1:
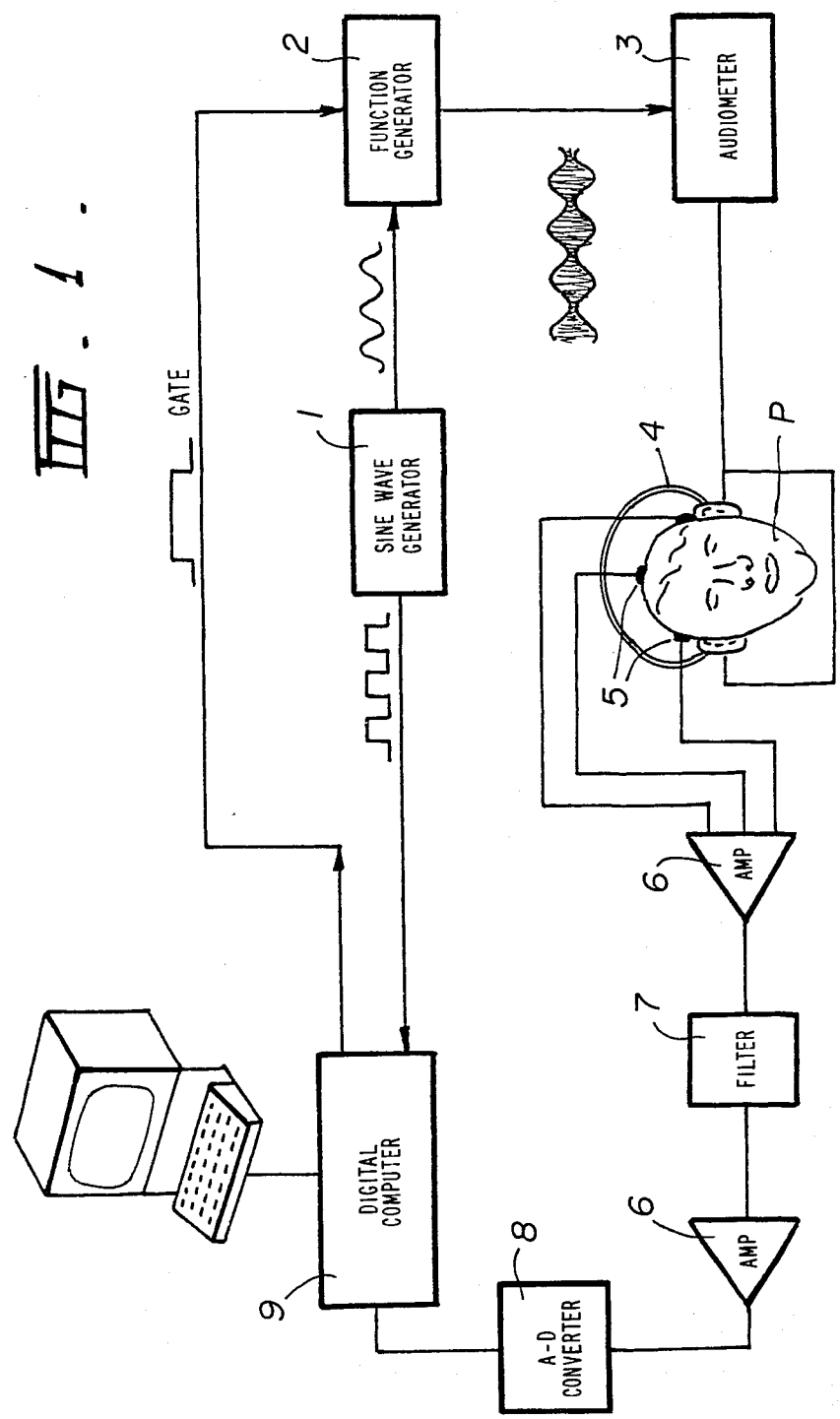
FIG. 1 is a schematic diagram of a preferred apparatus configuration embodying the invention.

Referring firstly to FIG. 1 of the drawings, the presently preferred experimental test apparatus configuration is shown schematically. The components of the apparatus are all well-known and widely used in audiometry and will therefore not be specifically described in greater detail than is shown in FIG. 1.

The experimental apparatus includes a stimulus section comprising a BWD sine wave generator capable of producing continuous sine and square waves in the frequency range 4 to 400 Hz. The sine wave output of the generator 1 is connected to a Datapulse 410 function generator 2 to provide the modulation envelope for an amplitude modulated sound, the carrier component of which is produced by the function generator 2 in the frequency range 100 to 10,000 Hz. The amplitude modulated signal is connected to the tape input of a Beltone 200C audiometer 3 for attenuation to headphones 4 for the patient P under investigation.

The apparatus also includes a recording section comprising silver/silverchloride electrodes 5 for positioning over the vertex and either mastoid of the patient P, the opposite mastoid acting as a ground reference. The electroencephalograph (EEG) detected by the electrodes 5 is amplified 100 dB by a Madsen BPA 77 biological amplifier 6, and then bandpass filtered by a Krohn Hite 3343 filter 7 having its cutoff frequencies set to half the modulating frequency (½ MF) and four times the modulating frequency (4 MF). The filtered signal is again amplified by a biological amplifier 6 and is sampled every 100 microseconds by a 14 bit analogue to digital converter 8, following which the sampled signal is inputted to a general purpose digital computer 9, such as a Hewlett Packard 2108B. The computer 9 is phase-locked to the stimulus signal by means of the square wave output of the sine wave generator 1 and the computer 9 is linked to the function generator 2 to apply gating signals to the function generator 2.

Figure 2:
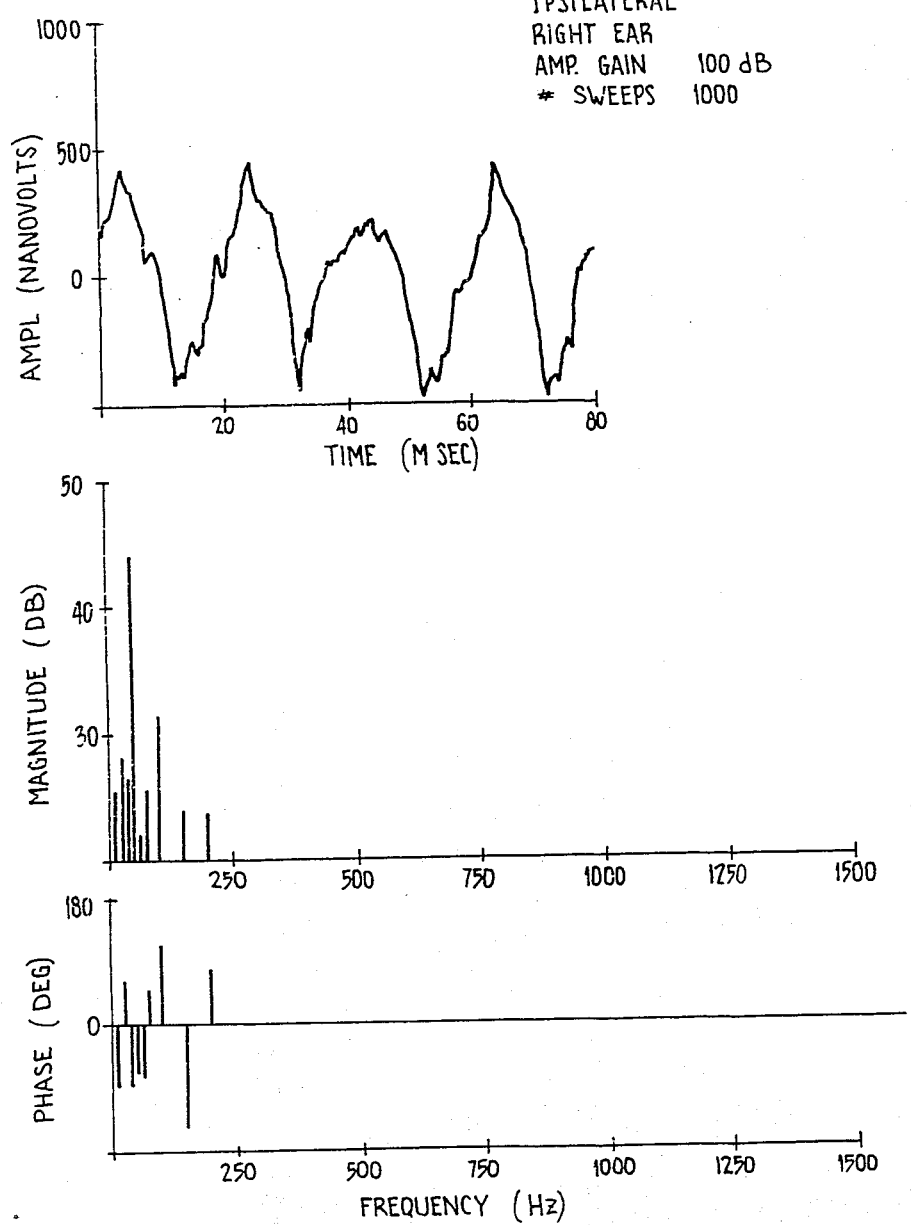
FIG. 2 shows typical recorded responses produced by the audiometer.

The analysis of the signal presented to the computer 9 is as follows. The computer 9 samples the EEG for four periods of the modulating envelope by detecting every fourth leading edge of the square wave output from the sine wave generator 1. At the end of each four periods, the computer 9 continues sampling but adds the data from each succeeding sampling period to the data from the preceding sampling period until from 200 to 2000 sampling periods have been collected to improve the signal to noise ratio to enable detection of a phase-locked periodic response in the patient's EEG. The total response is divided by the number of sweeps to give an average response. A typical average response is shown in FIG. 2 of the drawings. It will be noted that the response is periodic and has the same period as the modulation envelope. This represents a steady-state potential in the brain during the amplitude modulated stimulus.

At the end of each run, the raw average response is further analysed by the computer 9. Firstly, the number of data points are increased or decreased to 256 points by linear interpolation between adjacent points to the appropriate time position. Secondly, the new data is then analysed by fast Fourier transform to ascertain the amplitude and phase of the main components of the response. As will be seen in FIG. 2 of the drawings, the response has two main components: those at the modulating frequency and at two times the modulating frequency (first and second harmonics). It should be noted that the freqency of the response is not one of the frequencies in the stimulus spectrum. Since the fundamental frequency of the response is 50 Hz, it therefore cannot be an artefact.

Figure 3:
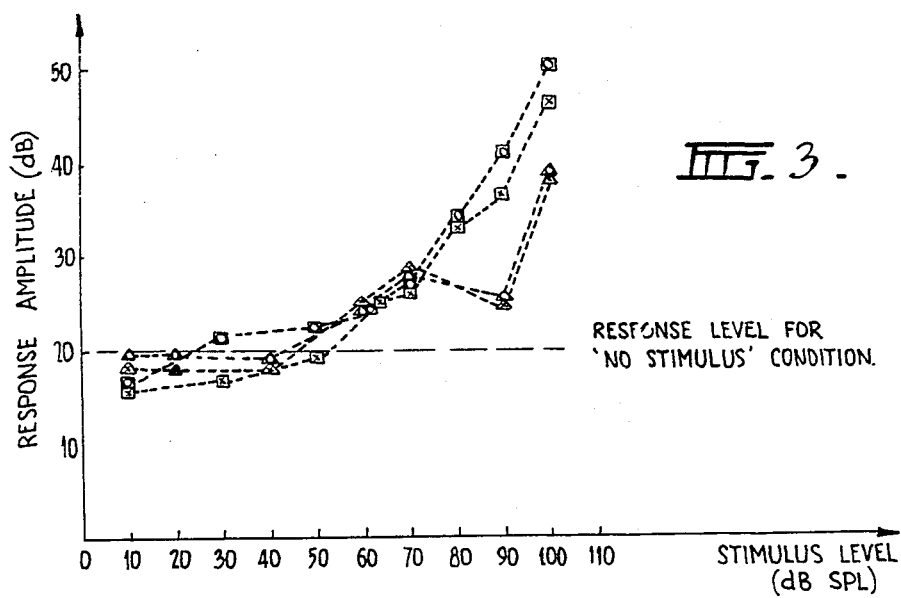
FIGS. 3 and 4 show plots of the response amplitude and phase for different sound pressure levels.
Figure 4:
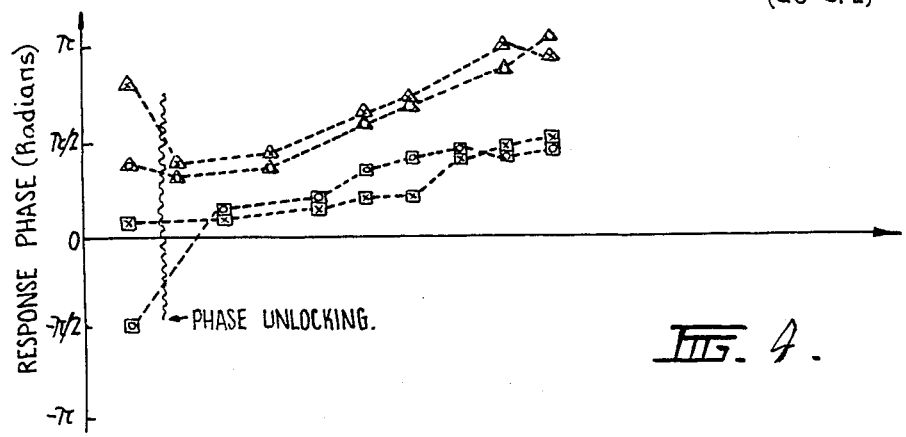

The above described audiometer may be used to test the sensitivity of the hearing of the patient by plotting the amplitude and phase of the response against the sound pressure level of the stimulus. FIGS. 3 and 4 of the drawings show typical plots from which it will be noted that the amplitude of the response increases with sound pressure level. In general, at modulation rates of less than 70Hz phase-locked responses could be recorded down to sound pressure levels of 20dB and the phase changes in a systematic fashion with sound pressure level. Below this level, the response becomes unlocked and the phase of the fundamental component of the response becomes random. The amplitude of the response increases with sound pressure level but at low levels is not significantly greater than the magnitude of the fundamental component in a "no stimulus" condition. At higher modulation rates (greater than 70 Hz) the magnitude of the response increases very rapidly at high sound pressure levels indicating a hyper-synchronous state in the brain. FIGS. 3 and 4 of the drawings show the variation in amplitude and phase for a 500 Hz tone modulated at 24 Hz and a 1000 Hz tone modulated at 64 Hz on the same patient. It has been found that the responses are not significantly affected by sedation and/or sleep and since the stimulus is, from an audiological point of view, very frequency specific, then the apparatus is likely to have clinical value in the objective testing of hearing in difficult to test patients, such as babies, young children and mentally retarded patients.

Figure 5:
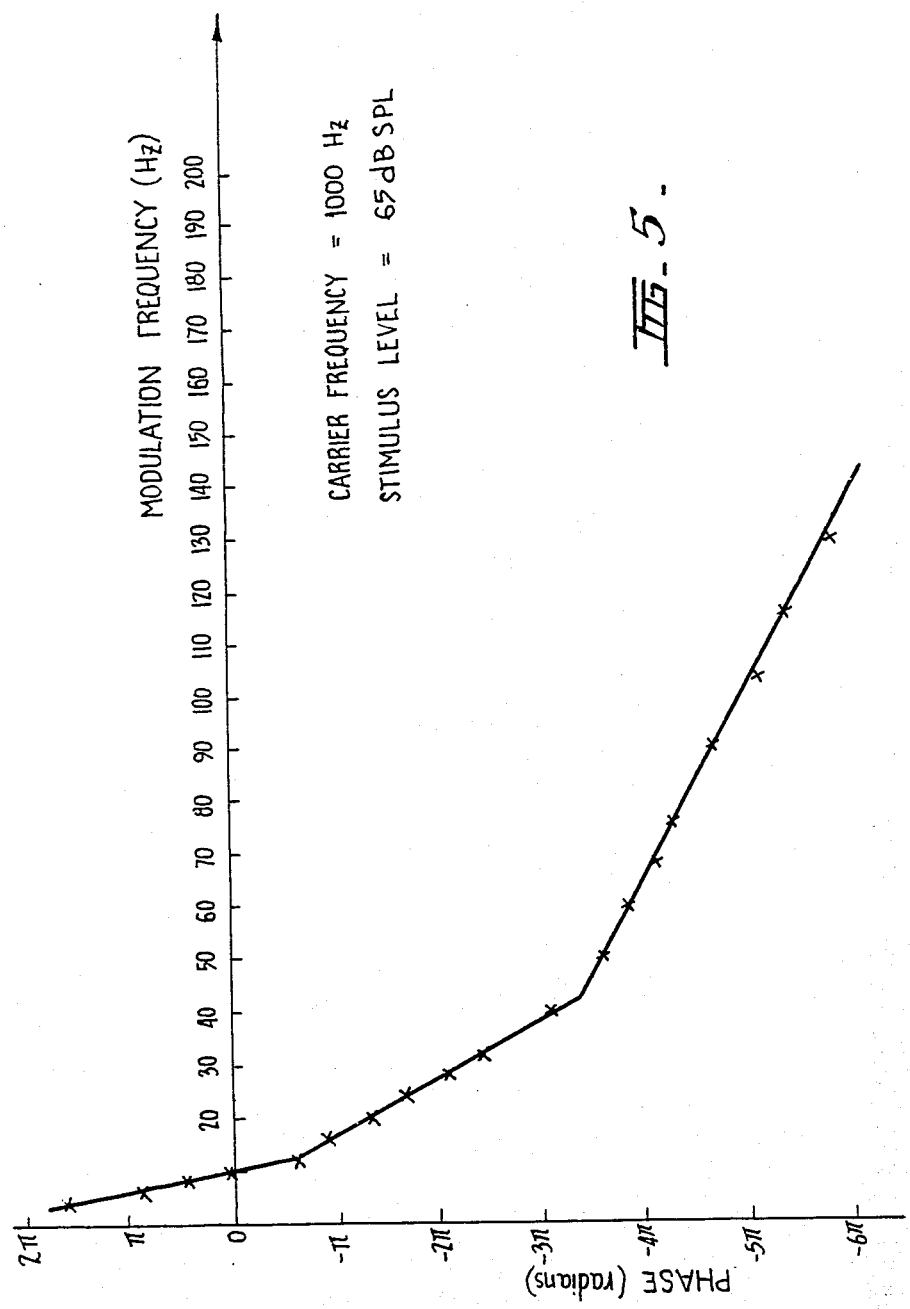
FIG. 5 shows a typical plot of the phase of one of the harmonic components of the response at different modulation frequencies.

The phase angle of the first and second harmonic components of the response is also plotted against changes in the modulation frequency. A typical plot showing the variation of phase angle of the fundamental component for a 1000 Hz carrier of 65 dB sound pressure level is shown in FIG. 5 of the drawings. In this case, the test signal was presented binaurally and the gradient of the lines gives the apparent latency of the response. It will be noted that at low rates of modulation, the latency is approximately 120 msec, in the middle rates 30 msec, and in the higher rates approximately 13 msec. Other latencies are obtained for different sound pressure levels and carrier frequencies. Similar patterns are seen when plotting the second harmonic of the response. In all, ten different latencies have been found which fall in the range of 3 to 130 msec suggesting brain stem and auditory cortex as the origin. The shorter latency responses (less than 40 msec) have been shown to be unaffected by sedation or sleep and accordingly the audiometer may be used in this mode to diagnose cerebral problems likely to affect the hearing, such as cerebral lesions.

It should be appreciated from the above description that the apparatus described above is experimental in nature and therefore will require modification before being suitable for wide spread clinical use. It is envisaged that the apparatus may be improved by applying the fast Fourier transform at the end of each sweep of four cycles of modulation and extracting the amplitude and phase at the modulating frequency and at twice the modulating frequency. The computer would then build up a distribution of the phase at these two frequencies and statisically test for phase locking. When phase locking occurs the computer would be programmed to automatically change the stimulus perameters such as the modulating frequency, carrier frequency and sound pressure level to more rapidly produce the necessary data. This improved procedure would markedly reduce the total analysis time to less than 1 hour thus making the technique clinically viable.

I claim:

1. An evoked response audiometer comprising means for supplying to the patient under investigation an auditory signal modulated by a continuous frequency waveform over a plurality of cycles of said waveform, to thereby evoke phase-locked steady state potentials in the brain of the patient, and means for recording evoked brain potentials evoked by said signal, whereby phase-locking of said steady state recorded potentials to the modulated auditory signal may be determined characterized in that said auditory signal is presented in a frequency specific continuous modulated form for an extended period of time to evoke phase-locked steady state potentials in the brain.

2. The audiometer of claim 1, wherein said auditory signal is amplitude modulated.

3. The audiometer of claim 2, wherein said modulation of said auditory signal is sinusoidal.

4. The audiometer of claim 1, 2 or 3, wherein said recording means includes means for sampling said potentials for a predetermined number of periods of the modulating wave, means for adding the sampled potentials to the previously sampled potentials, means for averaging the sampled potentials over between 200 and 2000 sampling periods, means for analysing the averaged potentials to determine the amplitude and phase of the main components of the averaged potentials and means for determining whether phase locking of said recorded potentials has occured.

5. The audiometer of claim 4, further comprising means for varying the modulating frequency, and means for determining the relationship between the phase of the main components of the response and the changes in modulating frequency from which the latency of the response may be estimated.

6. The audiometer of claim 4, further comprising means for varying the sound pressure level of the auditory signal, and means for analysing the responses obtained to record variations in the amplitude and phase of the response against changes in sound pressure level from which the sensitivity of hearing may be estimated.

7. A method of objectively testing the hearing of a patient, comprising the steps of presenting to the patient for an extended period of time an auditory signal modulated by a continuous frequency waveform over a plurality of cycles of said waveform to thereby evoke phase-locked steady state potentials in the brain of the patient, recording the brain potentials evoked by said signals, and analyzing said recorded potentials to determine whether they are phase-locked steady state potentials.

8. The method of claim 7, wherein said auditory signal is amplitude modulated.

9. The method of claim 7, wherein the modulating frequency of said auditory signal is varies and said brain potentials evoked by said varying signals recorded, said potential being further analysed to determine the relationship between the phase of the main components of the response and the modulation frequency from which the latency of the response may be estimated.

10. The method of claim 7, wherein the sound pressure level of the auditory signal is varied and the brain potentials evoked by said signals recorded, said potentials being further analysed to determine the relationship betwen the amplitude and phase of the response and the stimulus level from which the sensitivity of the hearing may be estimated.

* * * * *